United States Patent [19]

Vigo-Pelfrey

[11] Patent Number: 5,880,116
[45] Date of Patent: Mar. 9, 1999

[54] USE OF CELASTROL TO TREAT ALZHEIMER'S DISEASE

[75] Inventor: Carmen Vigo-Pelfrey, Mountain View, Calif.

[73] Assignee: Neurocal International, Mountain View, Calif.

[21] Appl. No.: 768,778

[22] Filed: Dec. 13, 1996

[51] Int. Cl.⁶ .................................................. A61K 31/56
[52] U.S. Cl. ........................ 514/178; 514/177; 514/168; 514/171
[58] Field of Search .................................. 514/168, 179, 514/177, 171

[56] References Cited

U.S. PATENT DOCUMENTS

| | | | |
|---|---|---|---|
| 4,328,309 | 5/1982 | Chalmers et al. | 435/126 |
| 4,746,674 | 5/1988 | Pierpaoli et al. | 514/415 |
| 5,192,753 | 3/1993 | McGeer et al. | 514/159 |
| 5,500,340 | 3/1996 | Lipsky et al. | 435/6 |

FOREIGN PATENT DOCUMENTS

WO 89/04659  6/1989  WIPO.

OTHER PUBLICATIONS

Li X.–Y, Anti–Inflam. Components of Tript. Wilfordii Hook F. (1993) Int. J. Immunotherapy IX(3): 181–187.

McGeer et al., Anti–Inflammatory drugs & Alzheimer's Disease, (1990) Lancet 335:1037.

Evans et al., Prevalence of Alzhemier's (1989) JAMA 262(18): 2551–56.

Reisberg, ed., Alzheimer's Disease (1983) Free Press Div of MacMillan, New York City, pp. 141–148.

Sulkava et al., Prevalence of Severe Dementia in Finland (1985) Neurology 35:1025–29.

Itagaki et al., Presence of T–cytotoxic suppresor . . . in Alzheimer's (1988) Neurosci. Lett. 91: 259–64.

Rogers et al., Expression of Immune Antigens . . . Relationship to Alzheimer's (1988) Neurosci. Ag. 9:339–49.

McGeer et al., Immune System Response in Alzheimer's Disease (1989) Can. J. Neurolog. Sci. 16:516–27.

McGeer et al. Activation of complement in Alzheimer patients (1989) Neurosci. Lett. 107:341–46.

Tachibana et al., Xenon Contrast Brain Changes in Alzheimer (1984) J. Gerontol. 39(4):415–23.

*Primary Examiner*—Theodore J. Criares
*Attorney, Agent, or Firm*—Barbara J. Luther

[57] ABSTRACT

The present invention provides a method for treating patients with Alzheimer's Disease which comprises administering a an effective amount of a celastrol formulation to the patients. One source of raw material for such a celastrol formulation is the root of the vine *tripterygium wilfordii* Hook F.

9 Claims, 5 Drawing Sheets

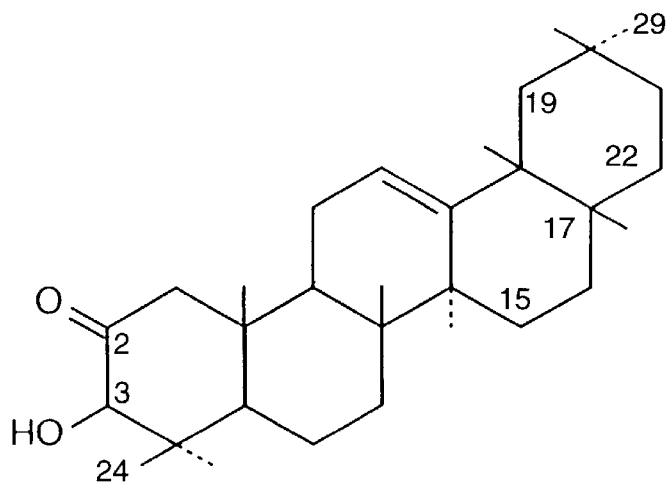
FIG._1
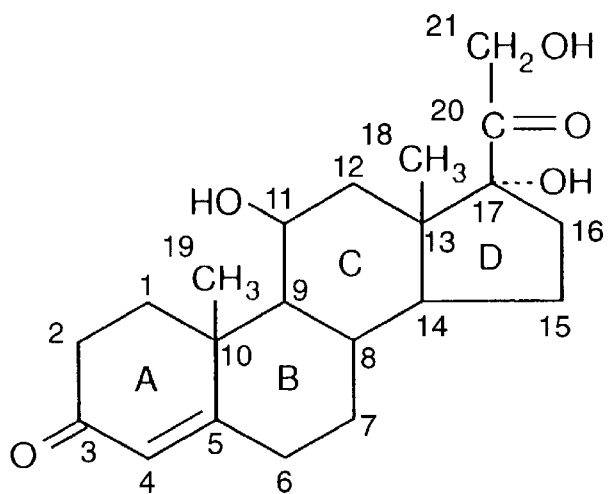
FIG._2
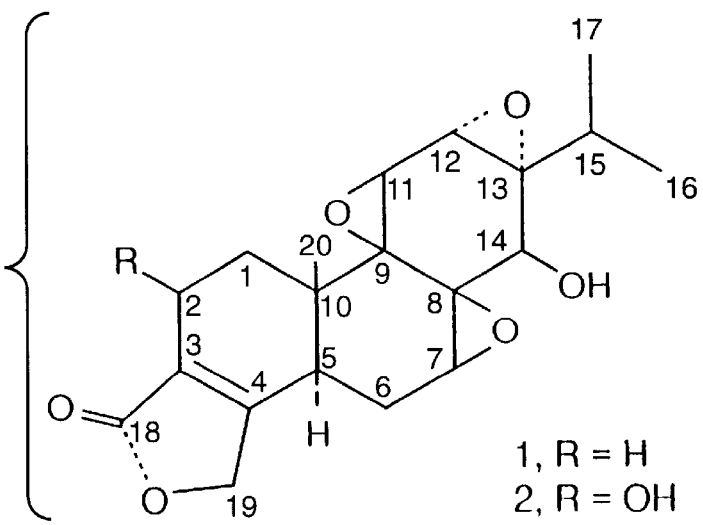
FIG._3
1, R = H
2, R = OH

FIG._4
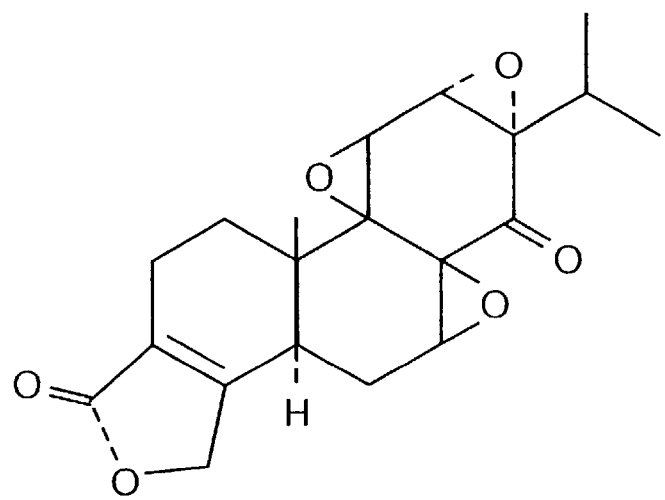
FIG._5
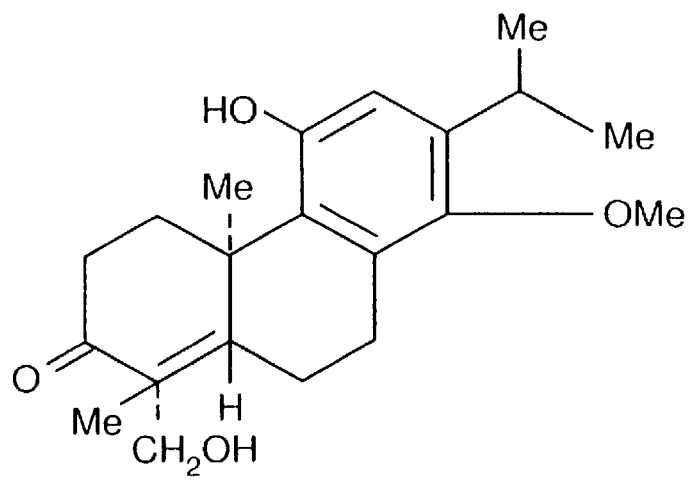
FIG._6
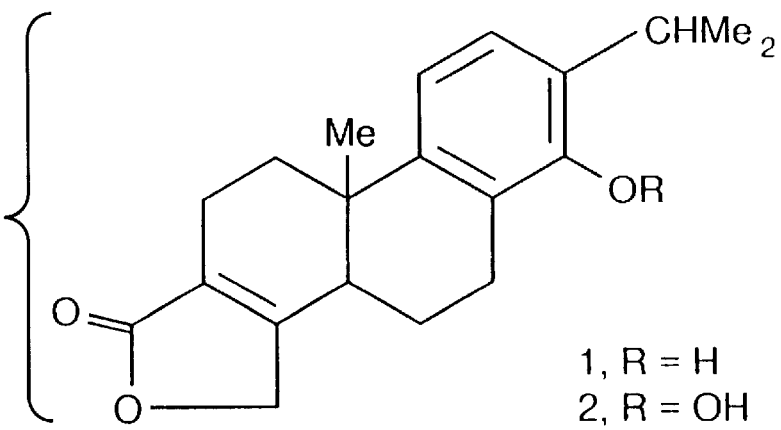
1, R = H
2, R = OH

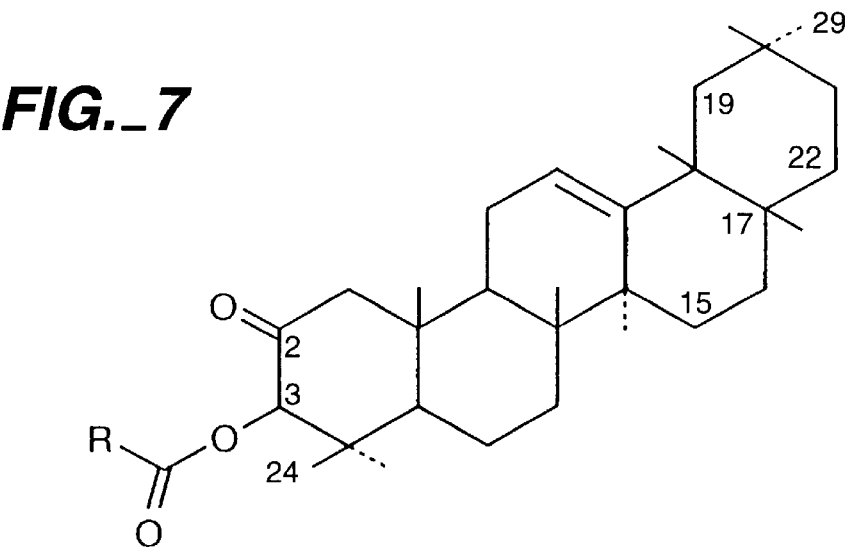
FIG._7
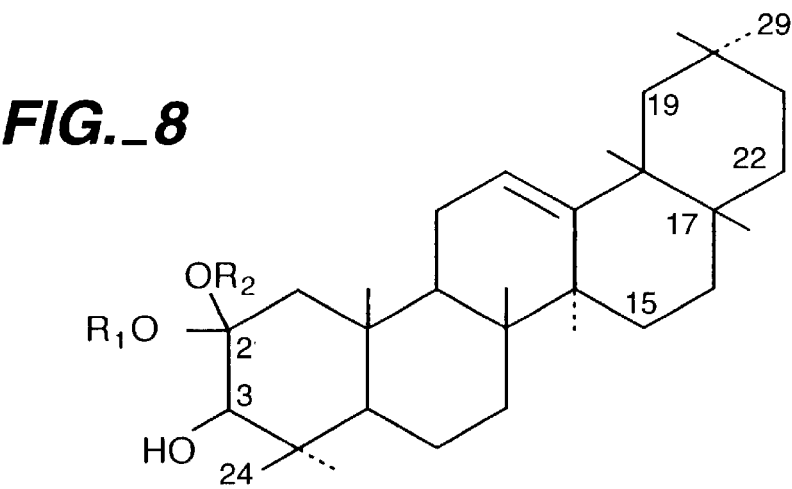
FIG._8
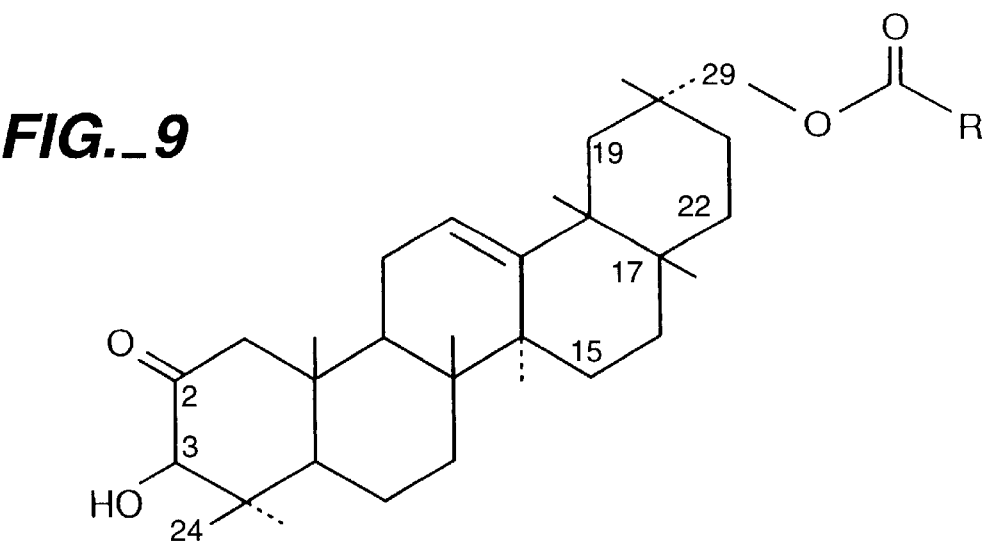
FIG._9

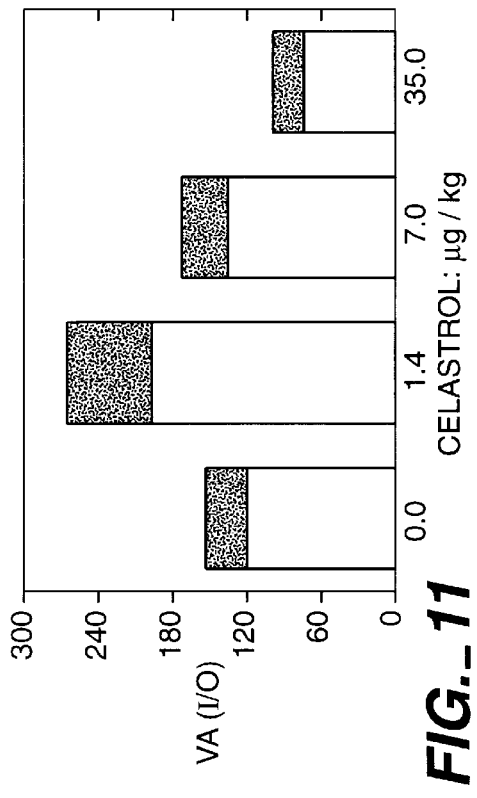
FIG._11
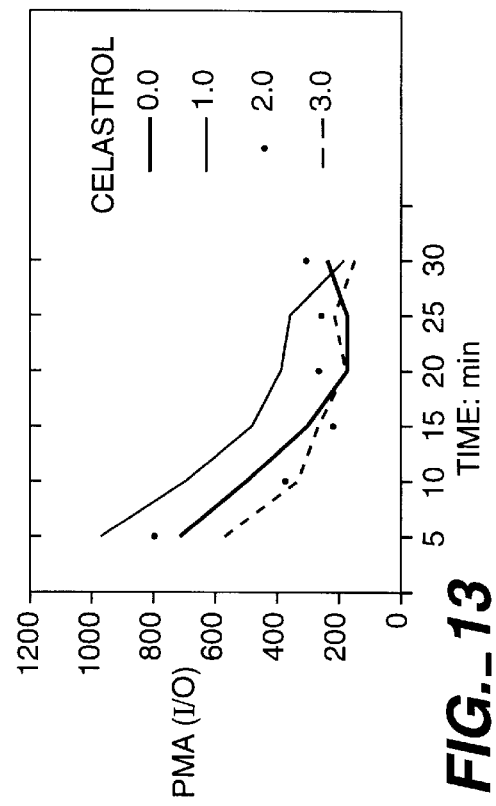
FIG._13
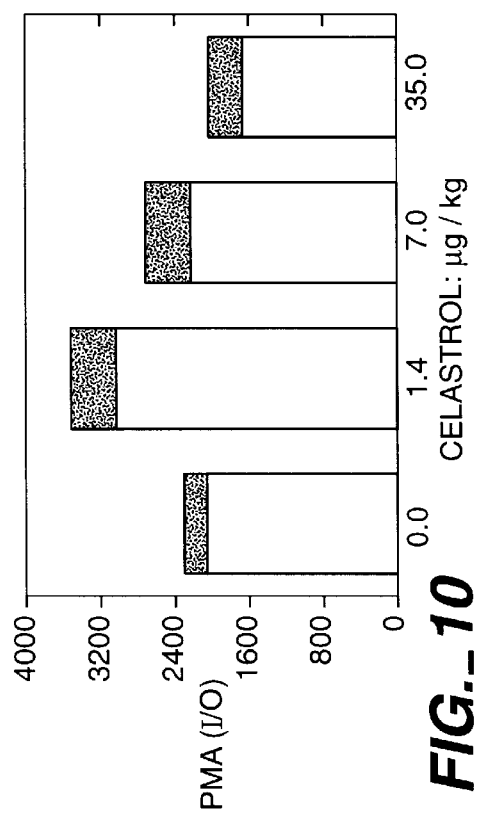
FIG._10
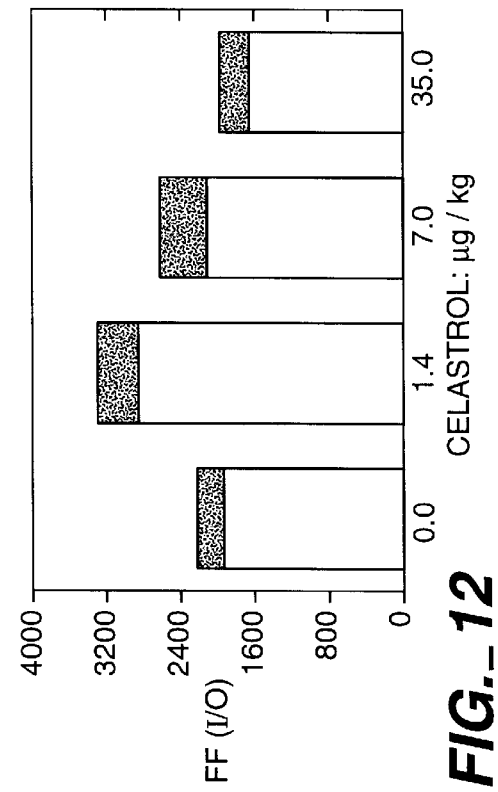
FIG._12

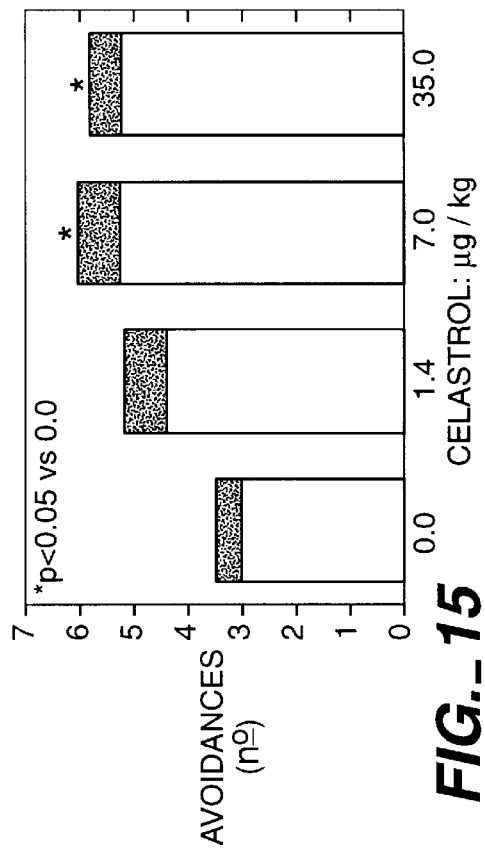
FIG._15
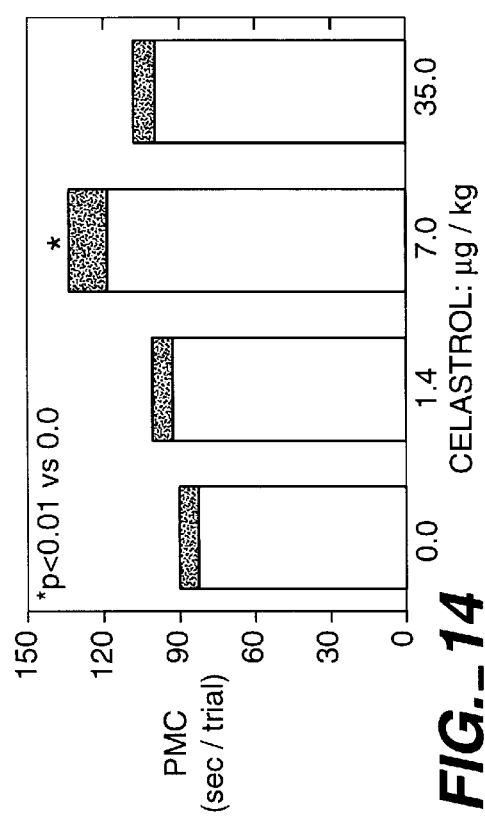
FIG._14
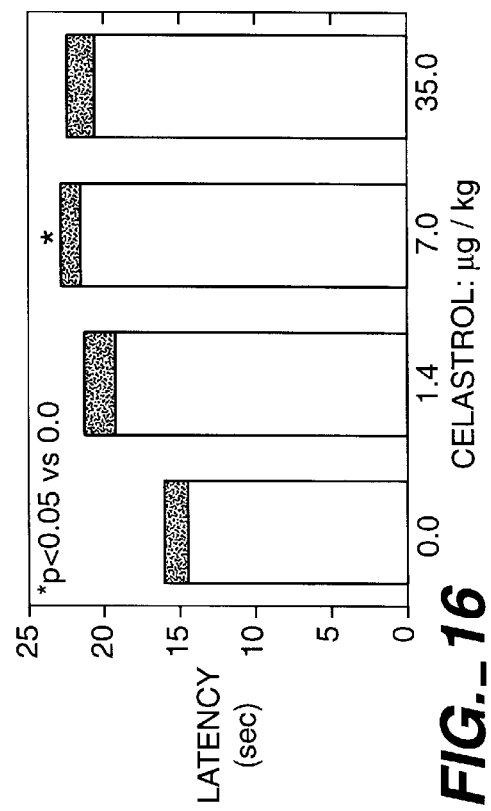
FIG._16

USE OF CELASTROL TO TREAT ALZHEIMER'S DISEASE

FIELD OF USE

The invention is in the field of medicinal treatment; more specifically, the invention is in the field of the treatment of Alzheimer's disease (AD) with celastrol, a steroid analog.

BACKGROUND OF INVENTION

Alzheimer's disease (AD) is a devastating condition of the later decades of life. The prevalence rate in a geographically defined US community were reported by Evans et al. (J. Amer. Med. Assn. 262:2551–56, 1989). Of individuals over 65 years of age, about 10.3% probably had AD. Stratified by decades, the prevalence was 3% for 65–74 years, 18.7% for 75–84 years and 47.2% for 85 and over. With the increasing age of the elderly population, the magnitude of the AD problem is expected to increase.

The criteria for diagnosing AD in the above-mentioned study included 1) a loss of intellectual abilities sufficient to interfere with social or occupational functioning and 2) neuropsychological testing with deficits in two or more areas of cognition. Deficits in neuropsychology tests can be a score of 2 or less on the delayed memory test, a score of 7 or less on the delayed recognition memory span test, or a decrease of two or more between immediate and delayed memory. In addition, there often is impairment in 1) language (a score of 10 or less on naming), 2) spatial ability (score of 5 or less on figure copying) and/or 3) abstraction (score of 6 or less on visual abstraction). The AD diagnosis also requires a history of no sudden onset of symptoms, a clear state of consciousness, and no hearing or visual impairment which could affect test results.

Although the etiology of AD is still being studied, the end-pathology is now well known, neuronal loss and the widespread appearance of neurofibrillary tangles and senile plaques. Some areas of the brain are more heavily involved, such as the temporal cortex and hippocampus, while the occipital cortex and cerebellum are much less affected. Large numbers of reactive microglia in affected regions of AD brains actively express HLA-DR of the major histocompatibility complex (MHC) (McGeer et al., Neurosci. Lett. 79:195–200, 1987). The classical function of HLA-DR is to present foreign antigen to the T-lymphocytic system. Thus, the causative process may be a cell-mediated immune reaction. McGeer et al. analyzed post-mortem brain tissue from AD and normal patients. The differences were striking: In the AD brains, but not the normal brains, activated leukocytes, reactive microglia/macrophages, reactive astrocytes, and T8 and T4 lymphocytes were observed. In both brains, antibody-mediated antigens (HLA-A,B,C) were prominent along the capillary lining cells. The AD-prominent cell types are all important actors in cell-mediated immunity: Reactive microglia express HLA-DR and send signals to activate the T-lymphocytic system, namely T-4 and T-8 lymphocytes. The T-4 cells bind to HLA-DR-expressing cells with antigen and stimulate a further response. The T-8 cells can help destroy cells with this complex and/or inhibit an antibody response. The presence of these various cell types (mainly located in the senile plaques) indicates an active chronic inflammatory process in AD (Itagaki, McGeer and Akiyama, Neurosci. Lett. 91: 259–64, 1988). The antigen which initiates this reaction still is not known; however, amyloid, paired helical filaments (PHF) and A68 are "foreign" proteins found in senile plaques and nowhere else, making them candidates for the causative antigen.

When AD brain and age-matched brain were examined for the presence of several complement components, McGeer et al (Neurosci. Lett. 107:341–346, 1989). reported that the classical complement pathway was activated in AD and that the amyloid deposits appeared to be made of unassembled C7 and C9 complement molecules. The classical pathway is activated by antibodies and a few enzymes, so the etiology is not firmly ascertained. The C9 complement complexes which cause cell lysis and death were found only on dystrophic neurites and neurofibrillary tangles and not on amyloid deposits. This indicates that some protein is being attacked on abnormal neurons.

Because of the apparent chronic immune reaction in AD, McGeer et al. expected to find an increased prevalence of AD in patients with rheumatoid arthritis, another chronic immune reaction. There was actually a relatively low prevalence of both AD and rheumatoid arthritis, which the authors proposed could be caused by rheumatoid patients taking anti-inflammatory agents on a chronic basis, particularly non-steroidal anti-inflammatory drugs (NSAIDs). McGeer et al. hypothesized that such NSAIDs also inhibited an inflammatory process which caused AD in other patients (McGeer et al. The Lancet 335:1037, 1990).

U.S. Pat. No. 5,192,753 to McGeer discloses the use of anti-rheumatoid NSAIDs in the treatment of AD. Five patients clinically diagnosed with early AD were entered into a six-month, open-label study with indomethacin, an NSAID. They were tested before and after by four neuropsychological tests: the Mini Mental Status Exam (MMSE), the Alzheimer Disease Assessment Scale (ADAS), the Boston Naming Test (BNT), and the Token Test (TT). In addition, at three months, the patients also underwent the MMSE and the ADAS. The neuropsychologists performing these tests did not know the patients' treatment regimens. One patient discontinued for failure to take medication. Although most parameters would be expected to deteriorate noticeably in AD patients during the six month interval, there was almost no change on the MMSE, a slight improvement on the BNT, and only slight decrements on the ADAS and the TT. These results were interpreted as successful treatment with an NSAID. In the file history, McGeer disclosed that other AD patients had received prednisone, a steroidal anti-inflammatory, which represented the steroid class. In the file history, McGeer et al. disclosed that prednisone had no effect.

To date, AD has no known prevention or cure. Treatment at this time is still palliative, consisting of proper nutrition, exercise and supervision of daily activity. Medication can help in reducing agitation and behavior problems. Propranolol, pindolol, buspirone and valproate have all been reported to help reduce agitation and aggression. Haloperidol and other high-potency dopamine-blocking agents may be used to control acute behavior disturbances. However, none of the proceesing improve memory or any of the underlying functional problems of AD. A subgroup of patients with AD shows improvement in cognitive and functional measures when treated with tacrine (COGNEX®, Parke-Davis Division of Warner-Lambert, Morris Plains N.J.), a potent centrally active, reversible acetycholinesterase inhibitor (Kaplan and Sadock, eds., CONCISE TEXTBOOK OF CLINICAL PSYCHIATRY, Williams & Wilkins, Baltimore, Md., 1996, p. 592)

What is needed is a drug which helps maintain or improve the mental status of AD patients, particular those functions associated with memory.

SUMMARY OF INVENTION

The present invention involves the use of a celastrol formulation in treating patients with Alzheimer's Disease.

In particular, the present invention provides for the oral administration of an effective amount of celastrol in a celastrol formulation to patients with Alzheimer's disease. Specifically, the invention provides for oral administration of celastrol in the range of about 0.2 to about 3 mg/kg/day.

In a particular embodiment, the celastrol formulation obtained by purifying the root of the vine *tripterygium wilfordii* Hook F, the formulation also containing other triterpenes besides celastrol.

DESCRIPTION OF FIGURES

FIG. 1 shows the chemical structure of celastrol.

FIG. 2 shows the chemical structure of a typical adrenocorticosteroid cortisol.

FIG. 3 shows the chemical structure of triptolide (1) and triptodiolide (2).

FIG. 4 shows the chemical structure of triptonide.

FIG. 5 shows the chemical structure of triptonoterpenol.

FIG. 6 shows the chemical structures of triptophenolide (1) and triptophenolide methyl ether (2).

FIG. 7 shows an ester pro-drug of celastrol.

FIG. 8 shows the celastrol core drug derivatized to an acetal-like form.

FIG. 9 shows an example of a hydroxylated and esterified form.

FIG. 10 is a bar graph displaying total activity by treatment group.

FIG. 11 is a bar graph displaying vertical activity by treatment group.

FIG. 12 is a bar graph displaying four-footed (FF) activity by treatment group.

FIG. 13 displays graph for the four treatment groups showing total activity for the thirty-minute test.

FIG. 14 is a bar graph displaying psychomotor coordination (PMC) by treatment group.

FIG. 15 is a bar graph displaying avoidances by treatment group.

FIG. 16 is a bar graph displaying latency time by treatment group.

DETAILED DESCRIPTION

Celastrol is a triterpene lactone epoxide compound, also known as a quinone-methide, whose structure is shown in FIG. 1. Celastrol is a steroid analog. For comparison, the general structure of adrenocorticosteroids is included as FIG. 2.

Celastrol has been isolated from a perennial twining vine *tripterygium wilfordii* Hook F. A procedure for isolating celastrol, triptonide and tripdiolide from the vine's roots is disclosed in U.S. Pat. No. 4,005,108. Over 60 components, including alkaloids, diterpenes and triterpenes have been isolated and identified from this plant. This vine has a long history in Chinese herbal medicine (Int. J. Immunotherapy IX(3):181–87, 1993) for the treatment of fever, chills, edema and inflammation.

Celastrol is an insecticidal inert red pigment and is isolated from the chloroform extract of the vine's root. In China, celastrol has been administered as a refined extract which contains predominantly triterpenes. Other triterpenoids from the vine include triptodiolide (FIG. 3), triptonide (FIG. 4), triptonoterpenol (FIG. 5), triptophenolide (FIGS. 6, 1) and triptophenolide methyl ether (FIGS. 6, 2). According to U.S. Pat. No. 5,500,340, the other triterpine constituents of the vine have been shown to have specific biological activity and may be useful individually or in combination with celastrol.

The refined extract (GTW) is extracted from the root xylem with water and then with chloroform. Next it is separated by column chromatography. Twenty-five grams of the xylem yield 1 mg of GTW, which contains only minute amounts of diterpenes and alkaloids, the main toxic constituents of the plant. GTW has been used to treat rheumatoid arthritis, chronic nephritis and various skin disorders. "Western-trained physicians have been using it increasingly to treat rheumatoid arthritis, chronic hepatitis, chronic nephritis, ankylosing spondylitis and various skin disorders, including psoriasis, systemic lupus erythematosus, allergic angitis, lepra reactions, etc. with more or less promising results (LiX.-Y, ibid., p. 181)." Recommended human doses for treatment of rheumatoid arthritis and systemic lupus erythematosus are 30–60 mg/day for an adult weighing 60 kg. Ibid. On the other hand, a Chinese prescription formulation which appears to provide 30 $\mu$g per tablet comes with the recommendation that two tablets be taken three times a day, which corresponds to a dose of 0.18 mg per day.

Celastrol is generally isolated from plants or plant cell culture with other triterpenes with similar structures. To meet future demand, it also may be necessary to chemically synthesize celastrol. In addition, celastrol can be converted by reaction with diazomethane, followed by column chromatography, to a methyl ester (pristimerin), which is sufficiently similar in structure to be expected to share many of the properties of celastrol, including its anti-inflammatory effects. Other related, pro-drug forms can be synthesized. For example, one can synthesize an ester pro-drug with the structure shown in FIG. 7 wherein R is highly variable, examples of which are given below. In another embodiment, one could derivatize the molecule through the C2 carbonyl to an acetal-like drug, as shown in FIG. 8, wherein R1 and R2 can be different or the same and are exemplified below. In addition, other carbons on the molecule can be hydroxylated and esterified, one example of which is shown in FIG. 9. The "R, R1 and R2" shown in FIGS. 7 to 9 are each independently H, lower alkyl, lower alkoxy, hydroxyalkyl, and hydrocarboxy-lower alkylene. Other convenient substitutions also are contemplated. All embodiments are conveniently tested according to the procedure given in Example 1.

The term "lower alkyl" as used herein refers to saturated monovalent hydrocarbon radicals having from 1 to 6 carbon atoms, for example, methyl, ethyl, propyl, isopropyl, butyl, hexyl, and the like.

The term "lower alkoxy" refers to radicals of the form OR, where R is lower alkyl as defined above. Suitable lower alkoxy radicals include methoxy, ethyoxy, propoxy, and the like.

The term "hydroxy-alkyl" refers to a lower alkyl group wherein one hydrogen atom is replaced with a hydroxy radical, for example, hydroxymethol, 2-hydroxyethyl, 1-hydroxyethyl, 3-hydroxypropyl, 2-methyl-2-hydroxyethyl, 3-hydroxypropyl, 2-methyl-2-hydroxypropyl, and the like.

The term (hydrocarboxy-lower alkylene" refers to radicals of the form $-(CH_2)_n COOH$, where n is an integer from 0 to 6. Suitable radicals include oxalyl, malonyl, succinyl, glutaryl and adipoyl.

Although exact contributions and strengths have not been determined, it has been suspected for some time that at least a portion of the activity of naturally derived celastrol preparations is also due to the accompanying triterpenes (see U.S. Pat. No. 5,500,340, Col 17, lines 1–16). Thus, when the term "celastrol formulation" is used, it is intended to include (1) purified celastrol from any natural or synthetic source, (2) the semi-purified GTW mixture, as well as the accompanying triterpenes, (3) other celastrol-enriched mixtures such as described in U.S. Pat. No. 4,328,309, and (4) other active celastrol analogs, as exemplified by FIGS. 7–9.

Since 1969, a number of clinical studies have been performed in China testing GTW. Effective treatment was reported in SLE, idiopathic nephritis, lupus nephritis, erythema multiforme, pemphigus, and rheumatoid arthritis. No effect was seen in hypertensive nephritis, which is not an inflammatory disorder. Side effects were poorly documented. However, at doses of 60–90 mg/day, gastrointestinal disturbances, including nausea, vomiting, anorexia, epigastric burning, xerostomia, diarrhea and constipation were observed. Some of these symptoms are common effects of the alkaloids and may be related to the residual alkaloids. Usually discontinuation of treatment was not necessary. Leukopenia and thrombocytopenia were observed in several patients, but cell counts rapidly recovered after stopping medication. Nevertheless, where leukopenia was caused by the primary disease state, such as RA or SLE, administration of GTW caused a recovery in the white blood cell count. Additional infrequent side effects include menstrual disturbances, oligospermia or azospermia, which recovered within two months of stopping therapy.

Celastrol has been tested in the laboratory for an immunosuppressive effect (ibid.): It inhibited proliferation in mice of splenic cells induced by mitogens PHA, Con A, LPS and PWM, with optimal effects at 0.1 μg/ml. In a test of ICR inbred mice, celastrol (1–3 mg/kg i.p. daily) reduced antibody formation very significantly and increased serum complement and decreased circulating immune complex levels. Celastrol decreased LPS-induced IL-1 production from peritoneal macrophages as well as Con A-induced IL-2 production from splenic lymphocytes in a dose dependent fashion. Also, in AA rats with experimental adjuvant arthritis, Celastrol reduced joint edema which may be correlated to the inhibition of lipid-peroxidation and free radical formation, which also were observed.

Among all the positive and negative effects of celastrol, there was no mention of any mental effects (Li, Int. J. Immunotherapy IX(3): 181–87, 1993).

In U.S. Pat. No. 5,500,340, Lipsky and Tao disclosed that acute and chronic toxicity studies had been performed in mice and rats. In mice the LD50 was 159.7±14.3 mg/kg. They also noted that the major chronic toxicity in rats given 30 mg/kg for 90 days was azospermia and decrease in testicular weight, but lower dosages did not cause decreases in testicular weight. Lipsky also noted that a typical daily dose in China is 0.8–1.5 mg/kg, which provides a reasonable safety index for patients. Lipsky and Tao disclose the administration of an extract containing celastrol to patients with rheumatoid arthritis. They reported that joint pain and mobility improved and remained improved even one month after cessation of treatment. Among side effects were skin rashes, diarrhea, anorexia, abdominal pain and amenorrhea. The side effects stopped after discontinuation of therapy. Few of the patients discontinued treatment because of side effects. They also reported a small study of SLE, in which the side effects of the extract were less than with previous treatment, such as corticosteroids and immunosuppressive agents, such as cyclosphophamide.

Non-steroidal anti-inflammatory drugs "NSAIDs" include such well known chemical entities as aspirin, ibuprofen and naproxen. The drugs are a recognized class for treatment of a wide range of chronic inflammatory conditions because they inhibit prostaglandin synthesis. Prostaglandins increase vascular permeability (leakage) in the postcapillary and collecting venules and cause vasodilatation. Thus, drugs inhibiting prostaglandin relieve pain and fever. In contrast, steroidal anti-inflammatory drugs are derivatives of naturally occurring human hormones, the adrenocorticosteroids. In this family are progesterone, desoxycorticosterone, corticosterone, cortisol, and 18-hydroxycorticosterone. All derive from cholesterol. The natural corticosteroids have sodium retention effects, cause liver glycogen deposition and exert an anti-inflammatory effect. Synthetic steroids such as prednisolone and triamcinolone have much less effect on sodium and far greater anti-inflammatory effect. Steroids also have effects on the brain, including mood, behavior and excitability. Most patients respond with an elevation in mood. In some, more definite mood changes occur, characterized by euphoria, insomnia, restlessness and increased motor activity. (GOODMAN & GILMAN'S THE PHARMACOLOGICAL BASIS OF THERAPEUTICS, 6th edition, The Macmillan Publishing Co., New York City, 1980. Pages 1470–93)

DEFINITIONS

The term "effective amount" refers to the amount of celastrol in a celastrol formulation that is necessary to improve the mental status of an individual with AD. The precise amount required will vary depending upon the particular compound selected, the age and weight of the subject, route of administration, and so forth, but may easily be determined by routine experimentation, as described below in the examples. In general, however, an effective amount will range from about 0.001 mg/kg to about 6 mg/kg, preferably about 0.002 mg/kg to about 3 mg/kg, more preferably about 0.002 mg/kg to about 2 mg/kg, and most preferably about 0.002 to about 1.5 mg/kg.

The term "improve the mental status of the AD patient" is readily determinable with standard tests (supra; MMSE, ADAS, BNT and TT) and even by observation of the individual in the home setting. There also may be a reduction in emotional outbursts and drug therapy which has been used to control those outbursts.

The term "pharmaceutically acceptable" refers to a compound, such as a salt or excipient, which is not unacceptably toxic to the subject to which it is administered. Pharmaceutically acceptable salts include inorganic anions such as chloride, bromide, iodide, sulfate, sulfite, nitrate, nitrite, phosphate, and the like, and organic anions such as acetate, malonate, pyruvate, propionate, cinnamate, tosylate, and the like. Pharmaceutically acceptable excipients are described at length by E. W. Martin, in REMINGTON'S PHARMACEUTICAL SCIENCES (Mack Pub. Co.).

Pharmaceutical compositions containing celastrol may contain one or more pharmaceutical carriers. The term "pharmaceutically acceptable carrier" refers to any generally acceptable excipient that is relatively inert, non-toxic and non-irritating. When the carrier serves as a diluent, it may be solid, semisolid, or liquid material acting as a vehicle, excipient, or medium for the active ingredient. Pharmaceutical unit dosage forms may be prepared for administration by any of several routes, including, but not limited to, oral and parenteral (especially by intramuscular and intravenous injection, or by subcutaneous implant or transdermal administration). Representative of such forms are tablets, soft and hard gelatin capsules, powders, lozenges, chewing gums, emulsions, suspensions, syrups, solutions, sterile injectable solutions, and sterile packaged powders. Composition containing celastrol may be formulated by procedures known in the art so as to provide rapid, sustained, or delayed release of any or all of the compounds after administration.

As the celastrol formulation of the present invention is well suited to oral administration, preferred carriers will facilitate formulation in tablet or capsule form. Solid pharmaceutical excipients such as magnesium stearate, calcium carbonate, silica, starch, sucrose, dextrose, polyethylene glycol (PEG), talc, and the like may be used with other conventional pharmaceutical adjuvants including fillers, lubricants, wetting agents, preserving agents, disintegrating agents, flavoring agents, and binders such as gelatin, gum arabic, cellulose, methylcellulose, and the like, to form admixtures which may be used as such or may be tabulated, encapsulated, or prepared in other suitable forms as noted above. A general description of formulation is given in REMINGTON'S PHARMACEUTICAL SCIENCES (Mack Pub. Co.).

ADMINISTRATION

Administration is preferably by oral dosage but may be by transdermal application, intranasal spray, bronchial inhalation, suppository, parenteral injection (e.g., intramuscular or intravenous injection), and the like. Carriers for parenteral administration include, without limitation, aqueous solutions of dextrose, mannitol, mannose, sorbitol, saline, pure water, ethanol, glycerol, propylene glycol, peanut oil, sesame oil, polyoxyethylene-polyoxypropylene block polymers, and the like. One may additionally include suitable preservatives, stabilizers, antioxidants, antimicrobials and buffering agents, for example, BHA, BHT, citric acid, ascorbic acid, tetracycline, and the like. Alternatively, one may incorporate or encapsulate the celastrol formulation in a suitable polymer matrix or membrane, thus providing a sustained-release delivery device suitable for implantation near the site to be treated locally. Other devices include indwelling catheters and devices such as the Alzet® minipump.

The invention has been disclosed by direct description. The following are examples showing the efficacy of the method in improving learning and memory. The examples are only examples and should not be taken in any way as limiting to the scope of the method.

EXAMPLE 1

Celastrol or vehicle was administered to rats as described below. Female Sprague-Dawley rats (obtained from Santiago University, Santiago de Compostela, Spain) were about 3 months old and weighed 200–250 g. The animals were maintained under standard conditions at the Euroespes Institute laboratory facilities.

The celastrol formulation was purchased in China in the form of pills under the name of "Leigongtengpian." The dose is expressed as the content of celastrol. The celastrol was dissolved in DMSO (35 $\mu$g/mL) and then adjusted to the appropriate concentration with 0.9% saline. Doses of 1.4, 7 and 35 $\mu$g/kg were administered intraperitoneally (i.p.) in a total injection volume of 2 ml/kg.

Immediately after injection, the animals were placed in the Osaka University Computerized Electronic Maze system (OUCEM-86, obtained from Bio Medica, Ltd., Osaka, Japan). The system, as previously described by Cacabelos et al (Prog. Med. 7:763–773, 1987), is integrated with the following components: A Programmable Electronic Platform (PEP) which measures 62 cm×62 cm and is equipped with 48 photo beam sensors (OPX-T30) to detect the three-dimensional position (four-footed, two-footed or rearing, and jumping) of the test animal; a Programming Panel (PP) (Model BECM-0064) for paradigm simulation; a Shock Generator Scrambler (SGS)(Model BSG-1065) to apply continuous or discontinuous electric currents to the PEP; a Control Station interface device to automatically computerize behavioral parameters; and a Computerized System (NEC PC-9801F) for data processing and experimental setting.

Tests were conducted in an open-field paradigm (where the rat can move freely) as previously described (Cacabelos et al. 1987) where psychomotor activity (PMA) was automatically recorded. Total PMA is the sum of horizontal and vertical movements. Horizontal movements are four-footed movements (FF). Vertical activity (VA) includes jumping and rearing (or two-footed) movements. The temporal profile of PMA during the 30 minutes of recording was also studied. PMA, FF and VA were expressed as total inputs/outputs (I/O). In general, increases in PMA, mainly in VA, are observed in situations of stress. A global increase in PMA is also found under treatment with stimulants and in rats with brain cholinergic deficits. Conversely, decreases in PMA are typical of sedative drugs, for instance.

At one hour after treatment, psychomotor coordination (PMC) was evaluated in a rota-rod apparatus (Letica Scientifiic Instruments, Barcelona, Spain) which consists of a roller turning at a constant pre-selected velocity (4–40 rpm) or at an increasing velocity with constant acceleration (for example, from 4 to 40 rpm in 300 seconds), and four digital counters that are stopped when the rat falls from the rod and lowers a pedal. In this test, the animals ran on a rod with constant acceleration until they fell off because they are unable to run at the necessary velocity to maintain equilibrium. Generally, there are two main causes of low performance in this test 1) myorelaxation and 2) balance disorders, as in some vestibular and brain lesions. Improved performance is seen with drugs improving muscular strength, motor coordination and/or balance. Mean running time of five consecutive trials was taken as an index of PMC.

Two hours after treatment, rats were tested for passive avoidance behavior in a PAB fixed-ratio maze paradigm, in which they learned to stay on a neutral platform (18×18 cm) in order to avoid a continuous electric footshock in the surrounding area during 10 trials (30 seconds each). The inter-trial interval was 30 seconds. The number of complete avoidances during 10 trials (Av; successful trials in which rat remains in the neutral area the entire 30-second period) and the latency per trial (La; time spent in the neutral platform before leaving it in a trial) were taken as learning indices. The number of avoidances represents a yes/no or discontinuous variable reflecting learning ability of the rats. In general, good learners perform more avoidances because they need fewer trials to learn to avoid footshock. Latency is a continuous variable measuring the time the rat is on the neutral platform without receiving footshock. Rats having the best memory or learning capacity spend more time on the neutral area. Therefore, latency is also an index of learning ability. Finally, when a drug increases the number of avoidances and mean trial latency in this paradigm, it means that this drug improves learning and memory function.

Data were statistically analyzed by the ANOVA and the Duncan test for multiple comparisons. Results were expressed as mean ± standard deviation (SD) in tables and as mean ± standard error of measurement (SEM) in figures.

Table 1 (below) shows the effects of celastrol on PMA, PMC and PAB learning in rats at the different doses of celastrol. The maximum effects of celastrol on PMA, PMC and PAB scores were observed with the 1.4 and 7 μg/kg doses, respectively. Although PMA for the 1.4 μg group was higher than for the untreated group, differences reached significance for the 7 μg groups for only PMC, AV and La and the 35 μg group for only La.

TABLE 1

Effects of celastrol on PMA, PMC and PAB learning in rats.

| Celastrol (μg/kg) | N | PMA (I/O) | PMC (sec/trial) | Av (n°) | La (sec) |
|---|---|---|---|---|---|
| 0.0 | 8 | 2050 ± 796 | 82.0±22.1 | 3.1±1.2 | 13.9±4.3 |
| 1.4 | 6 | 3011 ± 1185 | 99.4±19.2 | 4.3±2.1 | 18.3±5.2 |
| 7.0 | 6 | 2200 ± 1203 | 126.3±37.6** | 5.1±1.8* | 20.3±2.8* |
| 35.0 | 6 | 1637 ± 796 | 106.5±21.3 | 5.0±1.4* | 18.8±4.6 |

PMA: Psychomotor activity.
PMC: Psychomotor coordination.
PAB: Passive avoidance behavior.
Av: number of avoidances during 10 trials.
La: mean latency time per trial.
Results: X ± SD.
*$p < 0.05$ & **$p < 0.01$ vs control (0.0).

FIGS. 10–16 are graphical representations of this data. FIG. 10 shows the PMA for each treatment group. The 1.4 and 7 μg treatment groups fared somewhat better in this test, indicating possible increase in alertness, similar to that one would observe with stimulant treatment.

FIG. 11 displays the vertical activity (VA) for the different treatment groups. Again the 1.4 and 7 μg treatment groups fared somewhat better than the no-treatment group, again indicating an improvement in motor activity.

FIG. 12 displays the four-footed (FF) activity, which also was improved somewhat for the 1.4 and 7 μg groups. Four-footed activity indicates the level of coordinated motor activity the rat actually performs.

FIG. 13 shows the PMA over the thirty minute test interval. All treatment groups follow the normal pattern shown by the heavy solid line for the no-treatment group, i.e., a general trend of decreasing activity during the test period.

FIG. 14 displays psychomotor coordination (PMC) as evaluated in a rota-rod apparatus. The 1.4, 7 and 35 μg treatment groups all scored better than the no-treatment group, but only the 7 μg group result was statically significantly better than the untreated group ($p<0.01$). This improvement is similar to that seen with other drugs which improve muscular strength, motor coordination and/or balance.

FIG. 15 represents the numbers of complete avoidances during 10 trials. The 7 and 35 μg treatment groups scored significantly higher on this variable, indicating that they learned more quickly than the no-treatment group to avoid footshock.

FIG. 16 represents the latency time that the rats remained on the neutral platform without receiving footshock. The rats in the 7.0 μg/kg treatment group also learned significantly more quickly to stay on the platform and avoid the shock. This indicates significantly improved learning ability and memory.

EXAMPLE 2

Celastrol is administered to patients who have manifested an early stage of AD, as diagnosed by their own practitioner and confirmed by an independent board-certified neurologist. Two weeks before the clinical trial, the patients undergo appropriate psychoneurological tests such as the Mini Mental Status Exam (MMSE), the Alzheimer Disease Assessment Scale (ADAS), the Boston Naming Test (BNT), and the Token Test (TT). Neuropsychological tests are repeated on Day 0, 6 weeks and 3 months of the clinical trial. The tests are performed by neuropsychologists who are not aware of the patient's treatment regimen.

Patients are randomly assigned to celastrol treatment, placebo, or tacrine groups. The patients take celastrol at a dose of about 0.002 mg/kg to about 3 mg/kg/day by mouth (in one dose or divided between two or three doses) or a placebo or tacrine (for a treatment comparison). Patients may continue other pharmacological therapy for other conditions (e.g., treatment for diabetes, hypertension, etc.) and for palliative treatment of AD signs and symptoms. Optionally, for palliation, propranolol, pindolol, buspirone and valproate may be used to help reduce agitation and aggression. Haloperidol and other high-potency dopamine-blocking agents may be used to control acute behavior disturbances.

Scores are statistically compared among the treatment groups and at different intervals. Without treatment the natural course of AD is significant deterioration in the test scores during the course of the clinical trial. Celastrol-treated patients are considered improved if the patient's scores remain the same or improve during the clinical trial.

I claim:

1. A method of treating patients with Alzheimer's Disease which comprises administering to a patient in need thereof an effective amount of a formulation containing

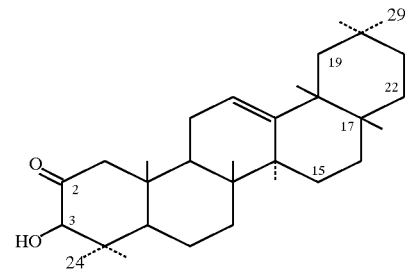

2. The method of claim 1 wherein administering the formulation comprises the method of oral administration.

3. The method of claim 2 wherein the effective amount of the compound of claim 1 is between about 0.002 and about 3 mg/kg/day.

4. The method of claim 1, wherein the compound shown in claim 1 is purified from the foot of the vine *tripterygium wilfordii* Hook F, said formulation containing other triterpenes besides celastrol.

5. The method of claim 1, wherein a prodrug of celastrol is administered.

6. The method of claim 1 wherein the celastrol is chemically synthesized.

7. The method of claim 2, wherein the patient is concomitantly administered other medications for Alzheimer's Disease to reduce agitation, behavior problems or acute behavior disturbances associated with Alzheimer Disease.

8. The method of claim 2, wherein the patient is concomitantly administered other medications to treat diabetes or hypertension.

9. The method of claim 5, wherein the prodrug is an ester of celastrol.

* * * * *

UNITED STATES PATENT AND TRADEMARK OFFICE
CERTIFICATE OF CORRECTION

PATENT NO. : 5,880,116
DATED : March 9, 1999
INVENTOR(S): Carmen Vigo-Pelfrey

It is certified that error appears in the above-identified patent and that said Letters Patent is hereby corrected as shown below:

Figures 1 and 5-9 are replaced as follows:

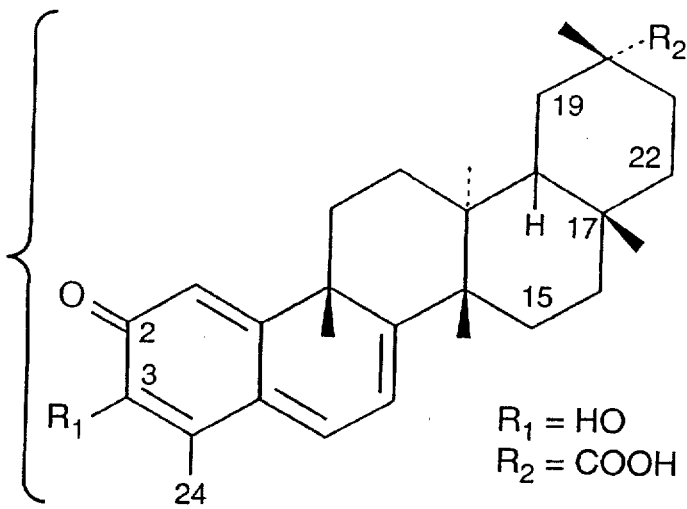

FIG._1

UNITED STATES PATENT AND TRADEMARK OFFICE
CERTIFICATE OF CORRECTION

PATENT NO. : 5,880,116
DATED : March 3, 1999
INVENTOR(S) : Carmen Vigo-Pelfrey

It is certified that error appears in the above-identified patent and that said Letters Patent is hereby corrected as shown below:

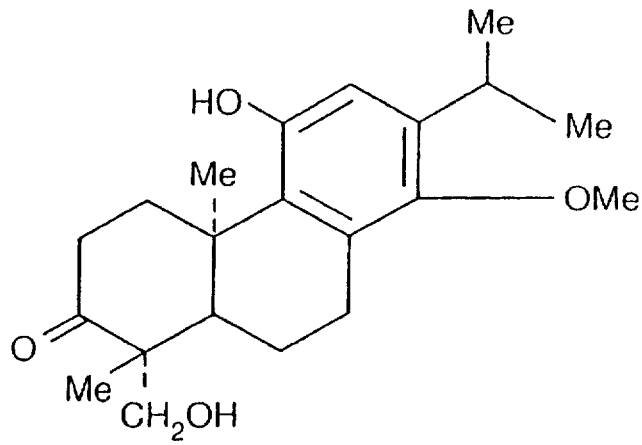

FIG._5

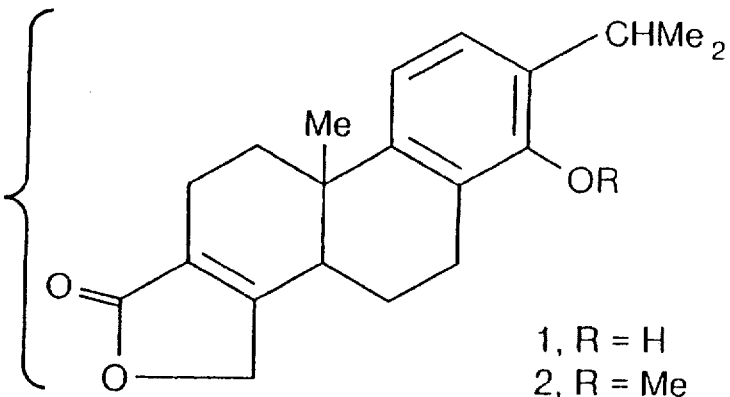

FIG._6

1, R = H
2, R = Me

UNITED STATES PATENT AND TRADEMARK OFFICE
CERTIFICATE OF CORRECTION

Page 3 of 5

PATENT NO. : 5,880,116
DATED : March 3, 1999
INVENTOR(S) : Carmen Vigo-Pelfrey

It is certified that error appears in the above-identified patent and that said Letters Patent is hereby corrected as shown below:

FIG._7

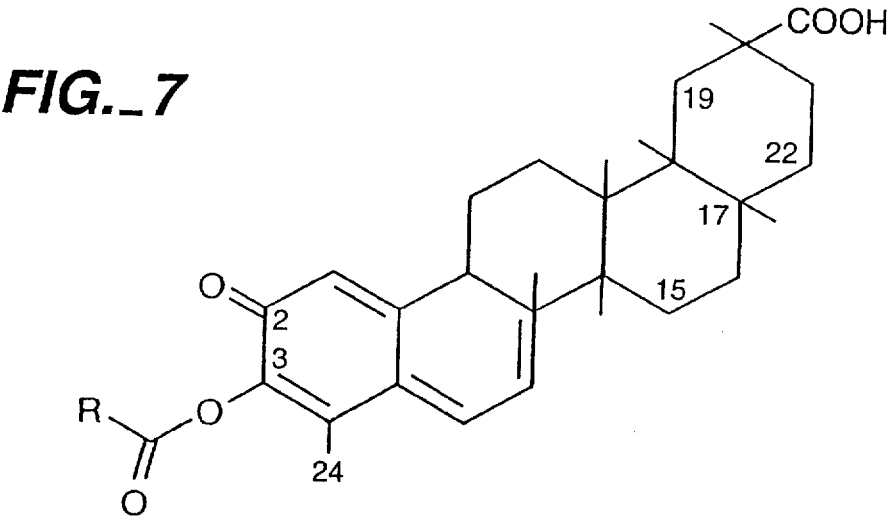

UNITED STATES PATENT AND TRADEMARK OFFICE
CERTIFICATE OF CORRECTION

Page 4 of 5

PATENT NO. : 5,880,116
DATED : March 3, 1999
INVENTOR(S) : Carmen Vigo-Pelfrey

It is certified that error appears in the above-identified patent and that said Letters Patent is hereby corrected as shown below:

FIG._8

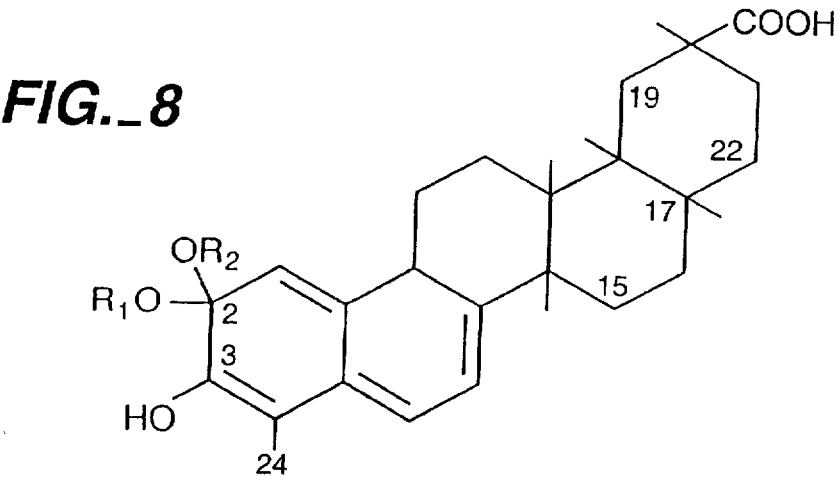

UNITED STATES PATENT AND TRADEMARK OFFICE
CERTIFICATE OF CORRECTION

Page 5 of 5

PATENT NO. : 5,880,116
DATED : March 3, 1999
INVENTOR(S) : Carmen Vigo-Pelfrey

It is certified that error appears in the above-identified patent and that said Letters Patent is hereby corrected as shown below:

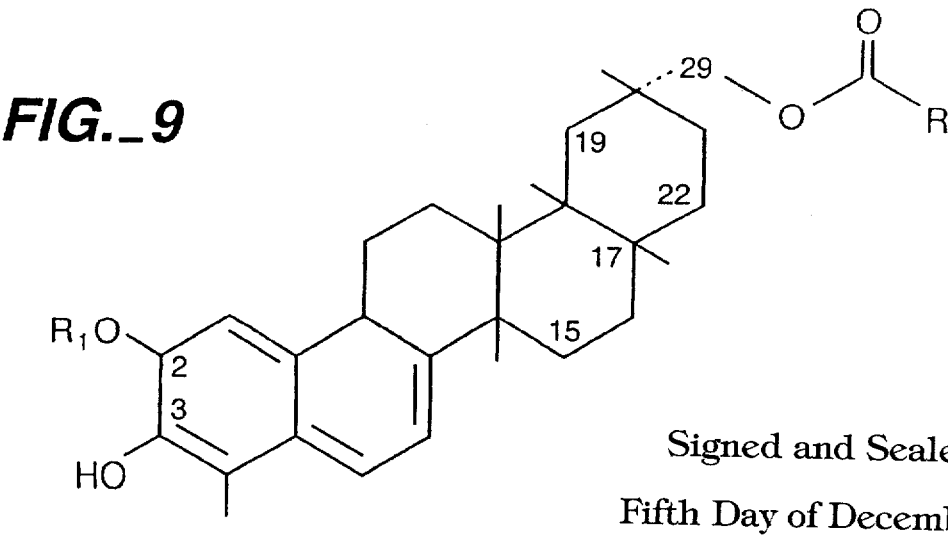

FIG._9

Signed and Sealed this

Fifth Day of December, 2000

Attest:

Q. TODD DICKINSON

Attesting Officer

Director of Patents and Trademarks